United States Patent
Suyama (10) Patent No.: US 11,287,641 B2
(45) Date of Patent: Mar. 29, 2022

(54) IMAGE PICKUP APPARATUS, ENDOSCOPE, AND METHOD FOR MANUFACTURING IMAGE PICKUP APPARATUS

(71) Applicant: OLYMPUS CORPORATION, Tokyo (JP)

(72) Inventor: Takuro Suyama, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/128,304

(22) Filed: Dec. 21, 2020

(65) Prior Publication Data

US 2021/0109337 A1    Apr. 15, 2021

Related U.S. Application Data

(63) Continuation of application No. PCT/JP2018/025511, filed on Jul. 5, 2018.

(51) Int. Cl.
  *G02B 23/24*  (2006.01)
  *A61B 1/00*   (2006.01)
  (Continued)

(52) U.S. Cl.
  CPC .......... *G02B 23/243* (2013.01); *A61B 1/0011* (2013.01); *A61B 1/00124* (2013.01);
  (Continued)

(58) Field of Classification Search
  CPC .............. G02B 23/243; G02B 13/0085; G02B 23/2476; A61B 1/0011; A61B 1/00124; A61B 1/00163; A61B 1/04; A61B 1/045; H01L 27/14625; H01L 27/14685; H04N 5/2253; H04N 5/2254; H04N 5/38; H04N 2005/2255
  See application file for complete search history.

(56) References Cited

U.S. PATENT DOCUMENTS

2004/0012698 A1  1/2004  Suda et al.
2010/0091168 A1* 4/2010  Igarashi ............ H01L 27/14685
                                             348/340

(Continued)

FOREIGN PATENT DOCUMENTS

EP     1239519 A2    9/2002
JP     2002-329849 A 11/2002
(Continued)

OTHER PUBLICATIONS

International Search Report dated Sep. 25, 2018 issued in PCT/JP2018/025511.

*Primary Examiner* — Jared Walker
(74) *Attorney, Agent, or Firm* — Scully, Scott, Murphy & Presser, P.C.

(57) ABSTRACT

An image pickup apparatus includes an image pickup member and a laminated optical member that is fixed in frame-shaped fixed areas around respective optical path areas. The fixed areas include a first area and a second area. A width of the first area is greater than a width of the second area. In the laminated optical member, an optical surface central axis deviates from an optical axis toward the first area. In the image pickup member, an image pickup surface central axis that is a central axis of a first main surface deviates from the optical axis.

4 Claims, 7 Drawing Sheets

(51) Int. Cl.
*A61B 1/04* (2006.01)
*H01L 27/146* (2006.01)
*H04N 5/225* (2006.01)
*H04N 5/38* (2006.01)

(52) U.S. Cl.
CPC ............ *A61B 1/00163* (2013.01); *A61B 1/04* (2013.01); *H01L 27/14625* (2013.01); *H01L 27/14685* (2013.01); *H04N 5/2253* (2013.01); *H04N 5/2254* (2013.01); *H04N 5/38* (2013.01); *H04N 2005/2255* (2013.01)

(56) References Cited

U.S. PATENT DOCUMENTS

| | | |
|---|---|---|
| 2012/0008934 A1 | 1/2012 | Kawasaki |
| 2016/0037029 A1* | 2/2016 | Igarashi ................. H05K 1/185 |
| | | 348/65 |
| 2017/0035279 A1* | 2/2017 | Fujii ...................... A61B 1/051 |

FOREIGN PATENT DOCUMENTS

| | | |
|---|---|---|
| JP | 2003-204053 A | 7/2003 |
| JP | 2012-18993 A | 1/2012 |
| JP | 2012-203195 A | 10/2012 |
| JP | 5951093 B1 | 7/2016 |
| JP | 2017-30252 A | 2/2017 |
| JP | 2017-32797 A | 2/2017 |
| WO | 2009/125654 A1 | 10/2009 |
| WO | 2017/022192 A1 | 2/2017 |

\* cited by examiner

IMAGE PICKUP APPARATUS, ENDOSCOPE, AND METHOD FOR MANUFACTURING IMAGE PICKUP APPARATUS

CROSS REFERENCE TO RELATED APPLICATION

This application is a continuation application of PCT/JP2018/025511 filed on Jul. 5, 2018, the entire contents of which are incorporated herein by this reference.

BACKGROUND OF THE INVENTION

1. Field of the Invention

The present invention relates to: an image pickup apparatus that includes a laminated optical member and an image pickup member; an endoscope that includes an image pickup apparatus including a laminated optical member and an image pickup member; and a method for manufacturing an image pickup apparatus that includes a laminated optical member and an image pickup member.

2. Description of the Related Art

In order to minimize invasion, the diameter of an endoscope has been reduced. Furthermore, for insertion into an ultra-small diameter lumen such as a blood vessel or a bronchiole, an ultra-small diameter endoscope is required.

U.S. Patent Application Publication No. 2012/0008934 discloses an image pickup apparatus composed of a wafer level laminate. This image pickup apparatus is manufactured by cutting after bonding a plurality of optical device wafers and a plurality of image pickup device wafers.

SUMMARY OF THE INVENTION

An image pickup apparatus of an embodiment includes an image pickup member and a laminated optical member. The image pickup member has a first main surface and a second main surface on an opposite side of the first main surface and includes an image pickup device, and an external electrode configured to output an image pickup signal is arranged on the second main surface. The laminated optical member has an incident surface which light enters and an emitting surface which is on an opposite side of the incident surface, a plurality of optical members are fixed in fixed areas around respective optical path areas, and the emitting surface is fixed to the first main surface. The emitting surface is larger than the first main surface. Each of the fixed areas is frame-shaped and includes: a first area closer to an optical surface central axis that is a central axis of the emitting surface than to an optical axis of the plurality of optical members; and a second area closer to the optical axis than to the optical surface central axis. A width of the first area is greater than a width of the second area. In the laminated optical member, the optical surface central axis deviates from the optical axis toward the first area. In the image pickup member, an image pickup surface central axis that is a central axis of the first main surface deviates from the optical axis toward where the external electrode is arranged.

An endoscope of the embodiment includes an image pickup apparatus. The image pickup apparatus includes an image pickup member and a laminated optical member. The image pickup member has a first main surface and a second main surface on an opposite side of the first main surface and includes an image pickup device, and an external electrode configured to output an image pickup signal is arranged on the second main surface. The laminated optical member has an incident surface which light enters and an emitting surface on an opposite side of the incident surface, a plurality of optical members are fixed in fixed areas around respective optical path areas, and the emitting surface is fixed to the first main surface. The emitting surface is larger than the first main surface. Each of the fixed areas is frame-shaped and includes: a first area closer to an optical surface central axis that is a central axis of the emitting surface than to an optical axis of the plurality of optical members; and a second area closer to the optical axis than to the optical surface central axis. A width of the first area is greater than a width of the second area. In the laminated optical member, the optical surface central axis deviates from the optical axis toward the first area; and in the image pickup member, an image pickup surface central axis that is a central axis of the first main surface deviates from the optical axis toward where the external electrode is arranged.

In a method for manufacturing an image pickup apparatus of the embodiment, the image pickup apparatus includes an image pickup member and a laminated optical member. The image pickup member has a first main surface and a second main surface on an opposite side of the first main surface and includes an image pickup device, and an external electrode configured to output an image pickup signal is arranged on the second main surface. The laminated optical member has an incident surface which light enters and an emitting surface on an opposite side of the incident surface, a plurality of optical members are fixed in fixed areas around respective optical path areas, and the emitting surface is fixed to the first main surface. The emitting surface is larger than the first main surface. Each of the fixed areas is frame-shaped and includes: a first area closer to an optical surface central axis that is a central axis of the emitting surface than to an optical axis of the plurality of optical members; and a second area closer to the optical axis than to the optical surface central axis. A width of the first area is greater than a width of the second area. In the laminated optical member, the optical surface central axis deviates from the optical axis toward the first area; and in the image pickup member, the image pickup surface central axis that is a central axis of the first main surface deviates from the optical axis toward where the external electrode is arranged. In dicing a laminated optical wafer in which the laminated optical member in plurality are arranged in matrix and the image pickup member in plurality are joined, a first side surface closer to the optical surface central axis than to the optical axis, among four side surfaces of each laminated optical member, is cut last for separation from the laminated optical wafer.

DETAILED DESCRIPTION OF THE PREFERRED EMBODIMENTS

First Embodiment

<Configuration of Endoscope>

Figure 1:
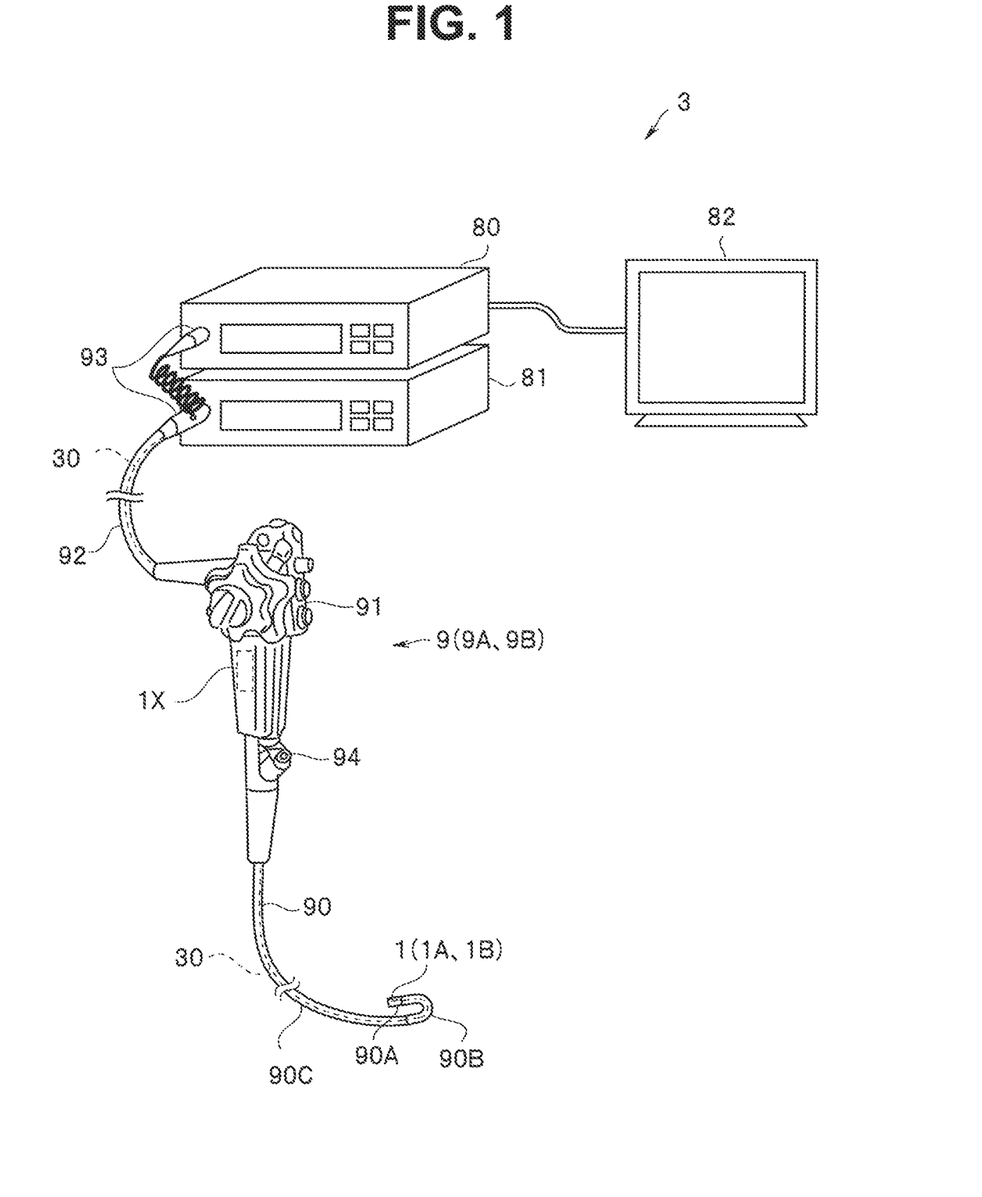
FIG. 1 is a perspective view of an endoscope in an embodiment.

As shown in FIG. 1, an endoscope system 3 including an endoscope 9 of an embodiment includes the endoscope 9, a processor 80, a light source device 81, and a monitor 82. For example, the endoscope 9 is configured so that a flexible insertion portion 90 is inserted into a body cavity of a subject and an in-vivo image of the subject is picked up and an image pickup signal is outputted.

At a proximal end portion of the insertion portion 90 of the endoscope 9, an operation portion (intermediate portion) 91 provided with various buttons for operating the endoscope 9 is arranged. The operation portion 91 has a treatment instrument insertion opening for a channel 94 for inserting biopsy forceps, an electric scalpel, an inspection probe, or the like into a body cavity of a subject.

The insertion portion 90 includes: a rigid distal end portion 90A where an image pickup apparatus 1 is arranged; a bendable bending portion 90B connected to a proximal end portion of the distal end portion 90A; and a flexible soft portion 90C connected to a proximal end portion of the bending portion 90B. The bending portion 90B is bent by an operation of the operation portion 91. The image pickup apparatus 1 transmits an image pickup signal through a signal cable 30.

A universal code 92 extending from the operation portion 91 is connected to the processor 80 and the light source device 81 via a connector 93.

The processor 80 controls the entire endoscope system 3, performs signal processing for an image pickup signal, and outputs the processed signal as an image signal. The monitor 82 displays the image signal that is outputted by the processor 80.

The light source device 81 includes, for example, a white LED. Illumination light emitted by the light source device 81 illuminates the subject by being guided to an illumination optical system (not illustrated) at the distal end portion 90A by passing through a light guide (not illustrated) that is inserted into the universal code 92 and the insertion portion 90.

As described later, the image pickup apparatus 1 has a small dimension in an optical axis orthogonal direction and therefore, the endoscope 9 including the distal end portion 90A having a thin diameter has a reduced invasion property.

Note that the endoscope 9 may be a rigid scope and may be for either medical or industrial application.

<Configuration of Image Pickup Apparatus>

Figure 2:
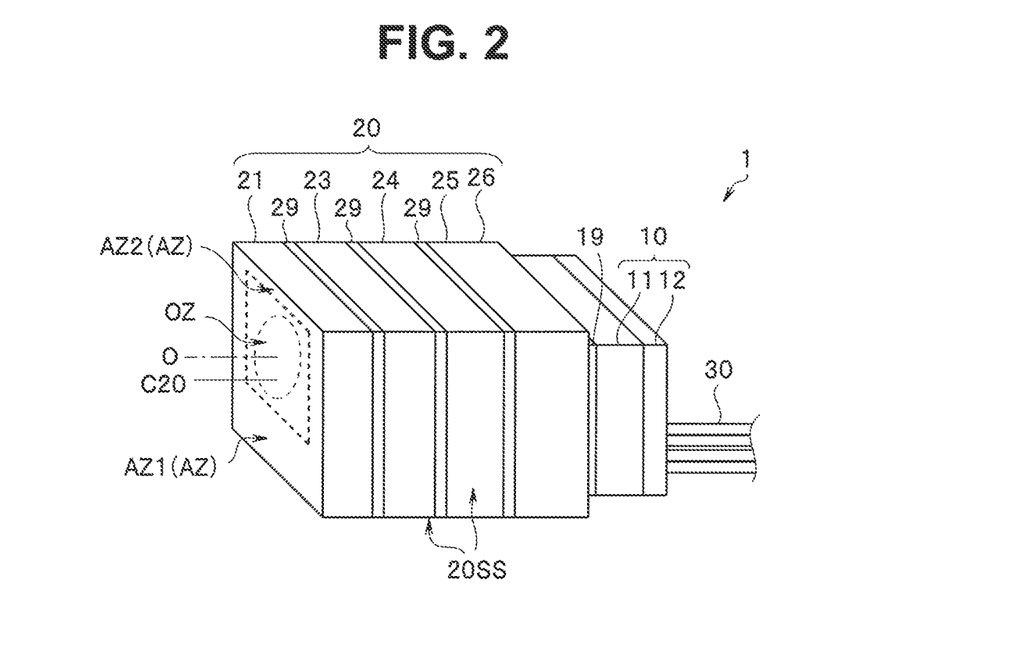
FIG. 2 is a perspective view of an image pickup apparatus in a first embodiment.
Figure 3:
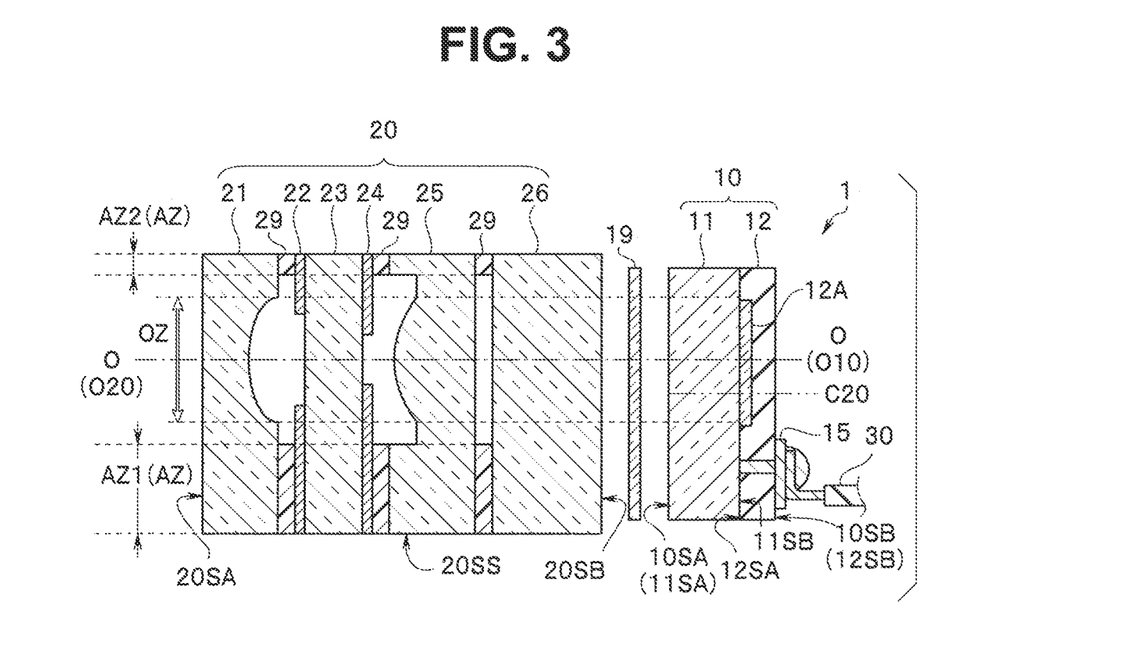
FIG. 3 is an exploded cross-sectional view of the image pickup apparatus of the first embodiment.

As shown in FIG. 2 and FIG. 3, the image pickup apparatus 1 of the embodiment includes an image pickup member 10 and a laminated optical member 20.

Note that in the following description, drawings based on embodiments are schematic ones and a relation between the thickness and width of each portion, the thickness ratio and relative angle between respective portions, and the like are different from actual ones. The drawings may include portions which are mutually different in a dimensional relation and ratio also among the drawings. In addition, illustration of some components and provision of reference signs may be omitted. A direction to the subject is referred to as "front."

The image pickup member 10 includes a cover glass 11 and an image pickup device 12. The cover glass 11 includes a front surface 11SA and a rear surface 11SB that is opposite to the front surface 11SA. The image pickup device 12 includes a front face 12SA and a back face 12SB opposite to the front face 12SA. The rear surface 11SB of the cover glass 11 is fixed to the front face 12SA of the image pickup device 12 by a joining layer (not illustrated).

The image pickup member 10 includes a first main surface 10SA (the front surface 11SA of the cover glass 11) and a second main surface 10SB opposite to the first main surface 10SA (the back face 12SB of the image pickup device 12); and on the second main surface 10SB, a plurality of external electrodes 15 are arranged.

The image pickup device 12 includes a light receiving unit (light receiving circuit) 12A composed of a CCD or CMOS image pickup circuit, on the front face 12SA; and the light receiving unit 12A is connected to a plurality of through wirings (not illustrated). The image pickup device 12 may be either a surface irradiation type image sensor or a rear surface irradiation type image sensor. The light receiving unit 12A is connected to the plurality of external electrodes 15 on the back face 12SB via respective through wirings (not illustrated). The plurality of external electrodes 15 are connected to a plurality of signal cables each of which transmits an image pickup signal.

The laminated optical member 20 in which a plurality of optical members 21 to 26 are joined includes an incident surface 20SA which light enters and an emitting surface 20SB that is on an opposite side of the incident surface 20SA. The emitting surface 20SB of the laminated optical member 20 is joined to the first main surface 10SA of the image pickup member 10 by a joining layer 19.

The optical members 21 and 25 are resin-molded lens wafers. The optical members 21 and 25 each may be a hybrid lens formed of parallel flat plate transparent glass where a resin lens is arranged; or may be a molded or injection-molded glass. The optical member 26 is a parallel flat plate filter formed of an infrared cut material that removes an infrared ray. The optical members 22 and 24 are apertures which are respectively arranged on both sides of a parallel flat plate glass 23. The optical members 21, 23, 25, and 26 are joined by sandwiching a joining layer 29 in between.

As described later, a side surface 20SS of the laminated optical member 20 that is a wafer level laminate is a cut surface and therefore, has cut traces. The cut traces are very small bumps and dips on the cut surface, which are caused by dicing processing, laser processing, sandblast, and etching processing.

Figure 4:
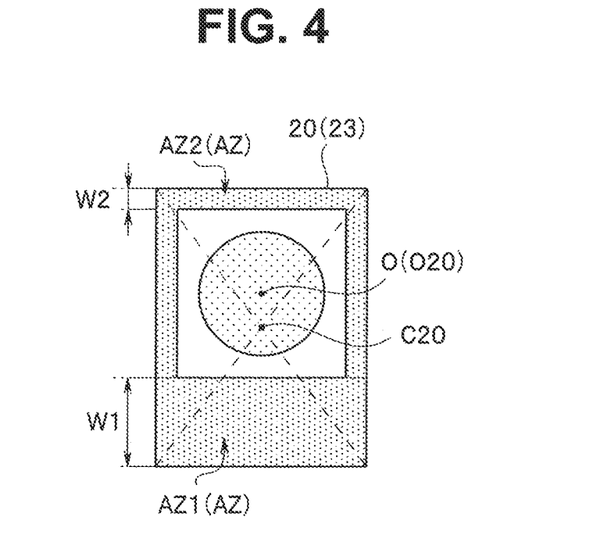
FIG. 4 is a front view of a laminated optical member of the image pickup apparatus of the first embodiment.
Figure 5:
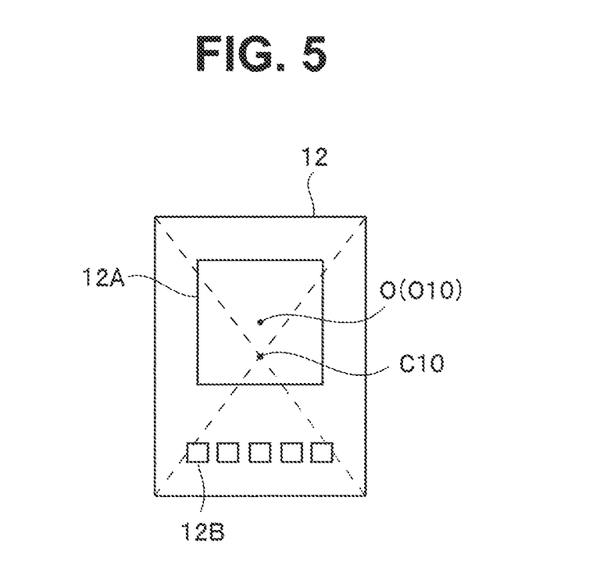
FIG. 5 is a front view of an image pickup device of the image pickup apparatus of the first embodiment.

As shown in FIG. 4 and FIG. 5, in the image pickup apparatus 1, the shapes of cross-sections orthogonal to an optical axis O for both the laminated optical member 20 and the image pickup member 10 are rectangular. For example, in the laminated optical member 20, the emitting surface 20SB (incident surface 20SA) is 800 μm×1200 μm and a length in the optical axis direction is 3000 μm. In the image pickup member 10, the first main surface 10SA (the second main surface 10SB) is 600 μm×1000 μm and a length in the optical axis direction is 300 μm.

The cross-sectional shape of an optical path area OZ of the laminated optical member 20 is circular. An optical surface central axis C20 that is a central axis of the laminated optical member 20 (a central axis of the emitting surface 20SB) deviates from a central axis O20 of the optical path area OZ, that is, the optical axis O. The optical surface central axis C20 passes through an intersection (barycenter) of two line segments each of which connects two opposite vertices among four vertices of the emitting surface 20SB of a rectangular shape, as shown in FIG. 4. In other words, in the laminated optical member 20, the optical axis O20 is offset from the optical surface central axis C20 that is the center of an outer shape of the laminated optical member 20.

As shown in FIG. 5, also in the image pickup member 10, an image pickup surface central axis C10 that is a central axis of the first main surface 10SA deviates from the optical axis O10 that is a central axis of the light receiving unit 12A. However, the optical axis O20 of the laminated optical member 20 and the optical axis O10 of the image pickup member coincide with each other, constituting the optical axis O of the image pickup apparatus 1.

As shown in FIG. 4, there is a fixed area AZ that is frame-shaped joined area, which is joined by optical members that are arranged to face each other and joining layers 29, around each of the optical path areas OZ of the plurality of optical members of the laminated optical member 20 (for example, the optical member 23).

The fixed area AZ is in a frame shape in which edge sides of four rectangular areas are connected. A first area AZ1 and a second area AZ2 among the four areas are opposed to each other across the optical axis O. In the laminated optical member 20, the optical axis O20 is offset from the center of the outer shape and therefore, in the fixed area AZ, a first width W1 of the first area AZ1 closer to the optical surface central axis C20 than to the optical axis O is greater than a second width W2 of the second area AZ2 closer to the optical axis O than to the optical surface central axis C20. For example, "the first area AZ1 is closer to the optical surface central axis C20 than to the optical axis O" indicates a state in which "the length of a virtual straight line connecting the optical surface central axis C20 and the first area AZ1 at a shortest distance is shorter than the length of a virtual straight line connecting the optical axis O and the first area AZ1 at a shortest distance." In addition, "the first width W1 of the first area AZ1" indicates "the length in the first area AZ1 of a virtual straight line connecting the optical axis O and the first area AZ1 at a shortest distance and extending in an outer peripheral direction."

In the image pickup apparatus 1, the image pickup surface central axis C10 deviates from the optical axis O10 that is the central axis of the light receiving unit 12A toward where the external electrodes 15 are arranged (see FIG. 5). However, the optical surface central axis C20 deviates from the optical axis O. Therefore, the image pickup apparatus 1 does not have a larger outer dimension in the optical axis orthogonal direction.

In addition, as already described, in the laminated optical member 20, the optical surface central axis C20 deviates from the optical axis O20 toward the first area AZ1 (see FIG. 4).

Furthermore, in the image pickup apparatus 1, the external electrodes 15 connected with the signal cables 30 that transmit an image pickup signal are arranged in an area of the second main surface 10SB opposite to the first area AZ1 of the fixed area AZ. A stress applied to the signal cables 30 is applied to the fixed area AZ through the external electrodes 15. Therefore, a larger stress is applied to the first area AZ1 than to the second area AZ2. However, the first area AZ1, which has a wider joining area due to its wider width, has a high joining strength.

Even when a stress is applied to the signal cables 30, there is no possibility of peeling of the fixed area AZ and therefore, the image pickup apparatus 1 is highly reliable.

If a defective image pickup device is included in an image pickup device wafer, it causes a defective image pickup apparatus to be manufactured. The image pickup apparatus 1 can use only an image pickup member 10 judged as a non-defective after being subjected to inspection; and therefore, achieves a high manufacturing yield.

In addition, although there are various kinds and small quantities of endoscopes, the image pickup apparatus 1 allows a plurality of kinds of image pickup apparatuses each including an image pickup device having different specifications to be simultaneously manufactured.

Furthermore, as described later, in dicing a laminated optical wafer 20W in which a plurality of optical device wafers are joined (see FIG. 8) into a plurality of the laminated optical members 20, peeling in the fixed area AZ2 in proximity to the optical path area OZ can be prevented.

Note that the fixed areas AZ are not limited to the joined areas in which opposed areas are joined with the joining layer 29 sandwiched in between. For example, a fixed area AZ may be a bonded area in which films formed of a metal or an inorganic material on opposed areas are directly bonded. In direct bonding, each of the opposed fixed areas is coated with a metal film or an inorganic material film such as a silicon oxide film; and after activation processing of a film surface, the both are fixed by thermocompression bonding. When the optical members are formed of, for example, glass (oxide silicon), direct bonding is possible without coating with a metal film or an inorganic film. In other words, at least one of the fixed areas AZ may be a bonded area in which a plurality of optical members are directly bonded.

At least one of the plurality of fixed areas is a joined area in which joining by the joining layer has been performed. In addition, at least one of the plurality of fixed areas is a bonded area in which direct bonding has been performed. In other words, the plurality of fixed areas of the laminated optical member 20 may include the bonded area and the joined area.

Figure 6:
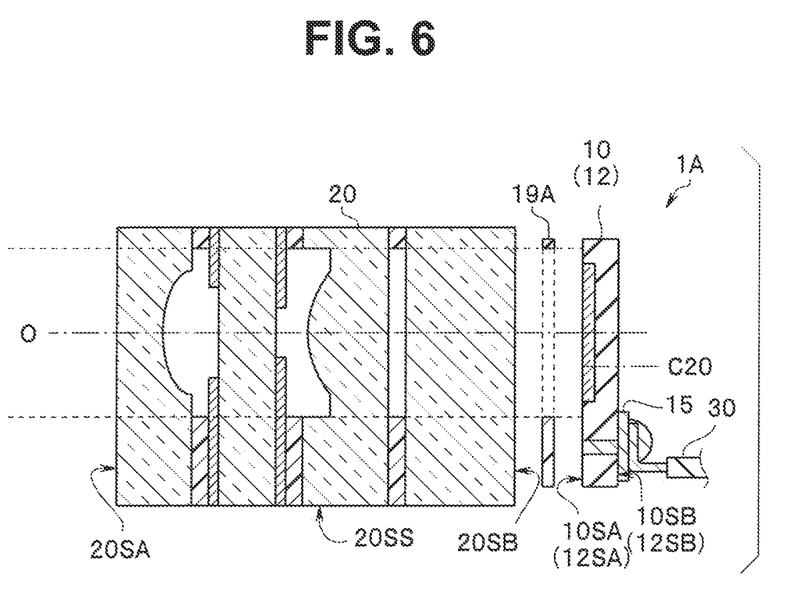
FIG. 6 is an exploded sectional view of an image pickup apparatus of a modification 1 of the first embodiment.

Note that as with an image pickup apparatus 1A of a modification 1 shown in FIG. 6, the joining layer 19 may also be patterned and the image pickup member 10 does not need to include the cover glass 11. In other words, the cover glass 11 is not an essential component required for the image pickup apparatus.

Although the laminated optical member 20 and the image pickup member 10 are directly joined in the image pickup apparatus 1A, both of them may be bonded or joined with a spacer sandwiched in between.

<Method for Manufacturing Image Pickup Apparatus>

Figure 7:
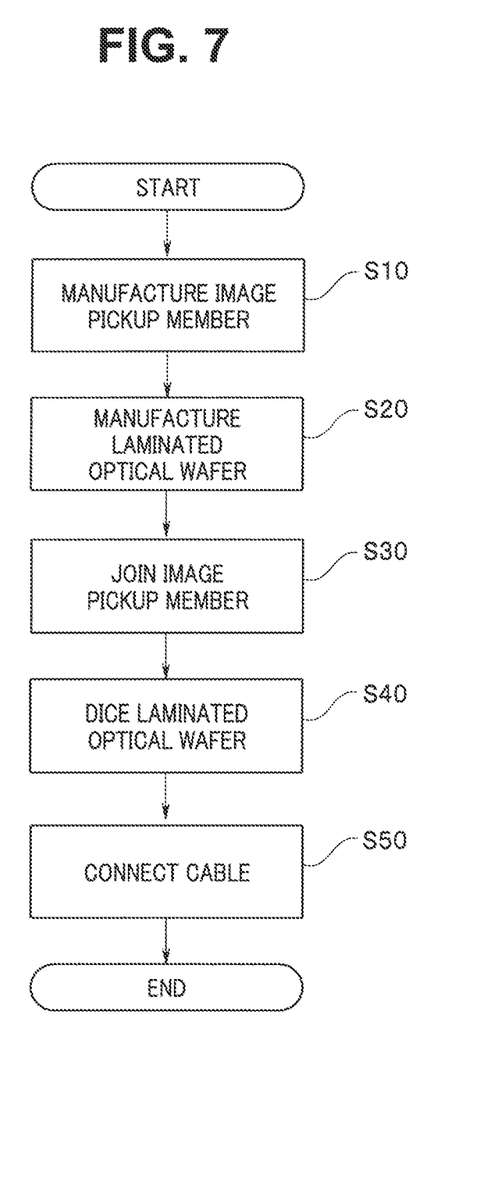
FIG. 7 is a flowchart for describing a method for manufacturing the image pickup apparatus of the first embodiment.

With reference to a flowchart in FIG. 7, a method for manufacturing the image pickup apparatus 1 will be described.

<Step S10> Image Pickup Member Manufacturing Step

Although not illustrated, by using a known semiconductor manufacturing technique for a silicon wafer, and the like, an image pickup device wafer on which a plurality of the light receiving units 12A and the like are arranged is manufactured. On the image pickup device wafer, a peripheral circuit that performs primary processing of an output signal of the light receiving unit 12A, performs processing of a drive control signal, and the like may be formed.

In order to protect the light receiving unit 12A of the image pickup wafer, for example, a cover glass wafer formed of a flat plate glass having a thickness of 250 μm is bonded or joined to the image pickup device wafer and thus, an image pickup wafer is manufactured. In the image pickup wafer, for example, an image pickup device wafer is subjected to a grinding process/polishing process so as to make its thickness 300 μm and after that, through wirings connected with the light receiving unit 12A and the external electrodes 15 of the second main surface 10SB are formed. The cover glass wafer bonds and seals the entire surface of the light receiving unit 12A so as to protect the light receiving unit 12A; however, it may bond and seal only a periphery of the light receiving unit 12A so that an air gap (space) is formed so as to be opposed to the light receiving unit 12A. Then, by dicing the image pickup wafer, the image pickup member 10 is manufactured.

It is preferable that an operation test of the image pickup device 12 be performed on the image pickup device wafer or the image pickup wafer and only the image pickup member 10 judged as a non-defective be used in subsequent steps.

<Step S20> Laminated Optical Wafer Manufacturing Step

Figure 8:
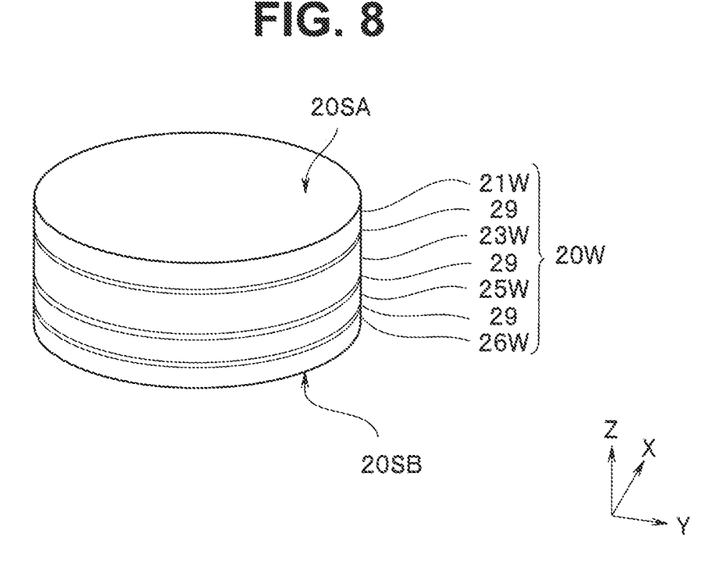
FIG. 8 is a perspective view of a laminated optical wafer for describing a method for manufacturing the image pickup apparatus of the first embodiment.

As shown in FIG. 8, optical wafers 21W to 26W on each of which a plurality of optical members are formed are manufactured. For example, the optical wafers 21W, 23W, and 25W are wafers formed of a parallel flat plate transparent material. The optical wafer 23W is a parallel flat plate filter wafer formed of an infrared cut material that removes an infrared ray. The filter wafer may be a transparent wafer or the like on a surface of which a bandpass filter that transmits only the light having a predetermined wavelength and cuts light having an unnecessary wavelength is arranged. The optical wafer 25W is a spacer wafer in which a portion for an optical path is a through hole. The optical wafers 21W and 23W may be hybrid lens wafers formed by arranging resin lenses 21L and 23L on glass wafers, respectively.

The configuration of the laminated optical wafer is not limited to the specifications of the embodiment but is set in consideration of its property and price according to the specifications of the laminated optical member 20. For example, the laminated optical wafer may be configured not to include a filter wafer.

As shown in FIG. 8, fixed areas AZ of the plurality of optical wafers 21W to 26W are joined by the joining layers 29 formed of an organic material (resin) or an inorganic material such as water glass, thereby manufacturing the laminated optical wafer 20W having a thickness of 3000 μm. Note that the kinds, thicknesses, number of laminated sheets, and lamination order of the plurality of optical wafers can be appropriately changed. In addition, as already described, at least one of the fixed areas AZ of the plurality of optical wafers 21W to 26W may be directly bonded.

<Step S30> Image Pickup Member Joining Step

On the emitting surface 20SB of the laminated optical wafer 20W (laminated optical member 20), a plurality of the image pickup members 10 (cover glasses 11) are joined by the joining layer 19. The image pickup members 10 may be directly bonded to the laminated optical wafer 20W.

<Step S40> Laminated Optical Wafer Dicing Step

Figure 9:
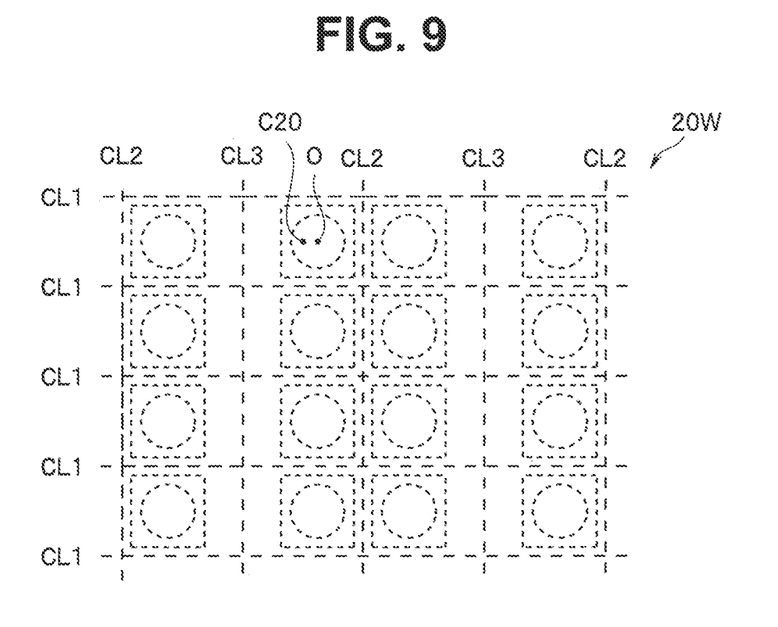
FIG. 9 is a top view of the laminated optical wafer for describing the method for manufacturing the image pickup apparatus of the first embodiment.

The laminated optical wafer 20W to which the plurality of image pickup members 10 are joined is cut by using a dicing saw, thereby being diced into a plurality of the laminated optical members 20. As shown in FIG. 9, on the laminated optical wafer 20W, adjacent two laminated optical members 20 of the plurality of laminated optical members 20 which are arranged in matrix are arranged so that optical path areas OZ are in proximity to each other.

In a dicing step, a first side surface closer to the optical surface central axis C20 than to the optical axis O, among the four side surfaces of each of the laminated optical members 20, is cut last.

More specifically, as shown in FIG. 9, the laminated optical wafer 20W is diced into the plurality of laminated optical members 20 by performing cutting along a cutting line CL1 and cutting along a cutting line CL2, and then, performing cutting along a cutting line CL3 last.

In the dicing step, peeling is likely to occur when the last cutting is performed. The cutting line CL3 is positioned farthest from the optical path areas OZ, among the plurality of cutting lines; and therefore, even when peeling occurs at a part of the fixed areas AZ, the optical path areas OZ are not easily affected. Thus, this manufacturing method achieves a high manufacturing yield of the laminated optical member 20.

The dicing step may be, for example, a step of cutting by laser dicing or a step of forming a cutting groove by sandblasting or etching.

It goes without saying that step S10 (image pickup member manufacturing step) may be performed after step S20 (laminated optical wafer manufacturing step). In addition, step S30 (image pickup member joining step) may be performed after step S40 (laminated optical wafer dicing step).

Furthermore, the image pickup wafer may be joined to the laminated optical wafer 20W without being diced into image pickup members and then, the laminated optical wafer on which the image pickup wafer has been joined may be diced. In other words, step S40 (laminated optical wafer dicing step) may be a step of dicing the laminated optical wafer on which the image pickup wafer has been joined.

<Step S50> Cable Connecting Step

The signal cables 30 are connected to the external electrodes 15 of the second main surface 10SB of each image pickup member 10. Note that an interconnecting wiring board may be bonded to the external electrodes 15 which are arranged in an area opposite to the first fixed area AZ1 and the signal cables 30 may be connected to the interconnecting wiring board.

According to the manufacturing method of the embodiment, a high-yield laminated optical member 20 can be manufactured.

Second Embodiment

An image pickup apparatus 1B of an embodiment is similar to the image pickup apparatuses 1 and 1A and has the same effect and therefore, components having the same functions are denoted by the same reference signs to omit their descriptions.

Figure 10:
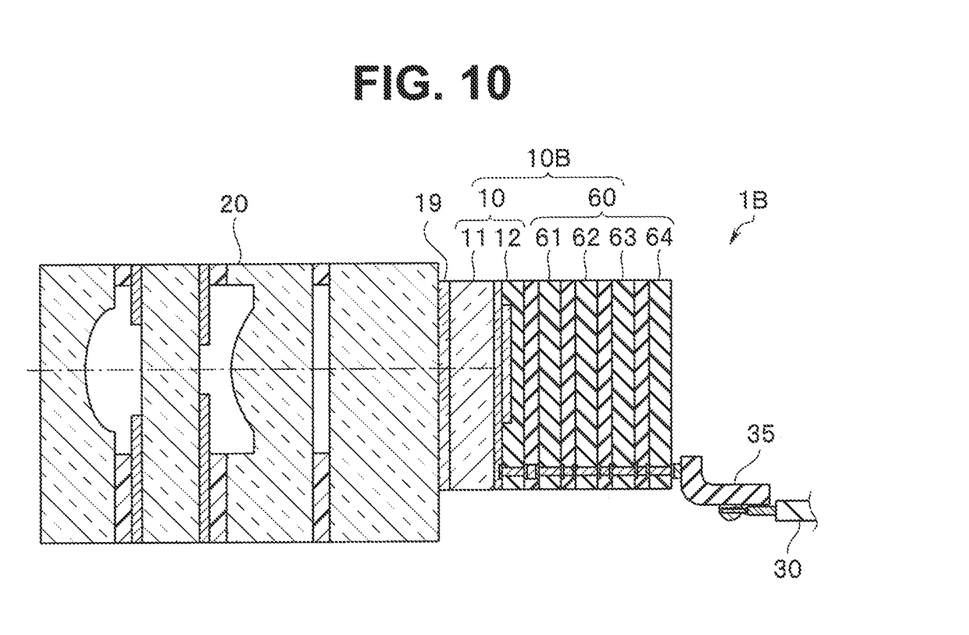
FIG. 10 is a cross-sectional view of an image pickup apparatus of a second embodiment.

As shown in FIG. 10, in the image pickup apparatus 1B, an image pickup member 10B includes a laminated device 60 bonded to an image pickup device 12. The laminated device 60 is bonded in a state where a plurality of semiconductor devices 61 to 64 are laminated.

The semiconductor devices 61 to 64 perform primary processing of an image pickup signal which is outputted by the image pickup device 12 and perform processing of a control signal that controls the image pickup device 12. For example, the semiconductor devices 61 to 64 include an AD conversion circuit, a memory, a transmission output circuit, a filter circuit, a thin-film capacitor, a thin-film inductor, and the like. The number of devices included in the laminated device 60 is, for example, three or more and ten or less. The plurality of semiconductor devices 61 to 64 are electrically connected with each other via a through wiring (not illustrated).

In a method for manufacturing the image pickup apparatus 1B, a plurality of device wafers on each of which a semiconductor device is formed are manufactured in addition to a cover glass wafer and an image pickup device wafer in manufacturing an image pickup member (S10). The device wafers include the plurality of semiconductor devices 61 to 64 each of which is an AD conversion circuit, a memory, a transmission output circuit, a filter circuit, a thin-film capacitor, a thin-film inductor, or the like.

By dicing the laminated device wafer in which the cover glass wafer, the image pickup device wafer, and the plurality of device wafers are laminated, the image pickup member 10B is manufactured.

The image pickup apparatus 1B includes the small-sized laminated device 60 that performs primary processing of an image pickup signal and therefore, achieves a higher performance than the image pickup apparatus 1 although it has the same or substantially the same size (outer dimension in the optical axis orthogonal direction) as the image pickup apparatus 1.

It goes without saying that endoscopes 9A and 9B including the image pickup apparatuses 1A and 1B, respectively have the effect of the endoscope 9 and also have the effects of the image pickup apparatuses 1A and 1B, respectively. Furthermore, the image pickup apparatuses 1, 1A, and 1B are not limited to an endoscope image pickup apparatus included in the endoscope 9 as long as they are ultra-small image pickup apparatuses including a wafer-level laminate.

The present invention is not limited to the above-described embodiments and modification, and the like; and various modifications, combinations, and applications are possible without departing from the spirit of the present invention.

What is claimed is:

1. An image pickup apparatus comprising:
   an image pickup member having a first main surface and a second main surface on an opposite side of the first main surface and including an image pickup device, an external electrode being arranged on the second main surface and configured to output an image pickup signal; and
   a laminated optical member having an incident surface and an emitting surface, light entering the incident surface, the emitting surface being on an opposite side of the incident surface, a plurality of optical members being fixed in fixed areas around respective optical path areas, the emitting surface being fixed to the first main surface, wherein
   the emitting surface is larger than the first main surface,
   each of the fixed areas is frame-shaped and includes a first area and a second area, the first area being closer to an optical surface central axis than to an optical axis of the plurality of optical members, the optical surface central axis being a central axis of the emitting surface, the second area being closer to the optical axis than to the optical surface central axis, a width of the first area being greater than a width of the second area,
   in the laminated optical member, the optical surface central axis deviates from the optical axis toward the first area, and
   in the image pickup member, an image pickup surface central axis that is a central axis of the first main surface deviates from the optical axis toward where the external electrode is arranged.

2. The image pickup apparatus according to claim 1, wherein the external electrode connected with a signal cable that transmits the image pickup signal is arranged in the second area opposite to the first area.

3. An endoscope comprising an image pickup apparatus, wherein the image pickup apparatus comprises:
   an image pickup member having a first main surface and a second main surface on an opposite side of the first main surface and including an image pickup device, an external electrode being arranged on the second main surface and configured to output an image pickup signal; and
   a laminated optical member having an incident surface and an emitting surface, light entering the incident surface, the emitting surface being on an opposite side of the incident surface, a plurality of optical members being fixed in fixed areas around respective optical path areas, the emitting surface being fixed to the first main surface, wherein
   the emitting surface is larger than the first main surface,
   the fixed area is frame-shaped and includes a first area and a second area, the first area being closer to an optical surface central axis than to an optical axis of the plurality of optical members, the optical surface central axis being a central axis of the emitting surface, the second area being closer to the optical axis than to the optical surface central axis, a width of the first area being greater than a width of the second area,
   in the laminated optical member, the optical surface central axis deviates from the optical axis toward the first area, and
   in the image pickup member, an image pickup surface central axis that is a central axis of the first main surface deviates from the optical axis toward where the external electrode is arranged.

4. A method for manufacturing an image pickup apparatus, wherein the image pickup apparatus comprises:
   an image pickup member having a first main surface and a second main surface on an opposite side of the first main surface and including an image pickup device, an external electrode being arranged on the second main surface and configured to output an image pickup signal; and
   a laminated optical member having an incident surface and an emitting surface, light entering the incident surface, the emitting surface being on an opposite side of the incident surface, a plurality of optical members being fixed in fixed areas around respective optical path areas, the emitting surface being fixed to the first main surface, wherein
   the emitting surface is larger than the first main surface,
   the fixed area is frame-shaped and includes a first area and a second area, the first area being closer to an optical surface central axis than to an optical axis of the plurality of optical members, the optical surface central axis being a central axis of the emitting surface, the second area being closer to the optical axis than to the optical surface central axis,
   a width of the first area is greater than a width of the second area,
   in the laminated optical member, the optical surface central axis deviates from the optical axis toward the first area, in the image pickup member, an image pickup surface central axis that is a central axis of the first main surface deviates from the optical axis toward where the external electrode is arranged, and in dicing a laminated optical wafer in which the laminated optical member in plurality are arranged in matrix and the image pickup member in plurality are joined, a first side surface closer to the optical surface central axis than to the optical axis, among four side surfaces of each laminated optical member, is cut last for separation from the laminated optical wafer.

\* \* \* \* \*